United States Patent [19]

Nakazato

[11] Patent Number: 5,378,835

[45] Date of Patent: Jan. 3, 1995

[54] METHOD OF PRODUCING WATER-SOLUBLE SODIUM PHEOPHORBIDE A

[75] Inventor: Masataka Nakazato, Yamanashi, Japan

[73] Assignee: S.L.T. Japan Co., Ltd., Tokyo, Japan

[21] Appl. No.: 123,387

[22] Filed: Sep. 20, 1993

Related U.S. Application Data

[63] Continuation of Ser. No. 760,451, Sep. 17, 1991, abandoned.

[30] Foreign Application Priority Data

Sep. 27, 1990 [JP] Japan ................................ 2-258136

[51] Int. Cl.$^6$ .......................................... C07D 487/22
[52] U.S. Cl. ..................................................... 540/145
[58] Field of Search .......................................... 540/145

[56] References Cited

U.S. PATENT DOCUMENTS

| | | | |
|---|---|---|---|
| 2,274,101 | 2/1942 | Snyder | 540/145 |
| 3,102,891 | 9/1963 | Allen | 540/145 |
| 4,604,241 | 8/1986 | Sakata et al. | 540/145 |
| 4,634,557 | 1/1987 | Sato | 540/145 |

FOREIGN PATENT DOCUMENTS 61-83185  4/1986  Japan ................................ 540/145

*Primary Examiner*—Floyd D. Higel
*Attorney, Agent, or Firm*—Lowe, Price, Leblanc & Becker

[57] ABSTRACT

A producing method of phosphoric a applied in medical treatment comprises dissolving sodium hydroxide in n-propyl alcohol, isopropyl alcohol or mixtures thereof so as to prepare a solution of the sodium hydroxide, dissolving the pheophorbide a in a solvent miscible with the sodium hydroxide solvent so as to prepare a solution of the pheophorbide a and dissolving the solution of the pheophorbide a in the solution of the sodium hydroxide so as to obtain sodium pheophorbide a. Thus, the water-soluble pheophorbide a can be safely used.

6 Claims, 2 Drawing Sheets

METHOD OF PRODUCING WATER-SOLUBLE SODIUM PHEOPHORBIDE A

This application is a continuation of application Ser. No. 07/760,451 field Sep. 17, 1991, now abandoned.

BACKGROUND OF THE INVENTION

1. Field of the Invention

This invention relates to a producing method of pheophorbide a which causes photosensitivity in human and animals and which is used in photoradiation therapy against cancer and the like.

2. Prior Art

Photoradiation therapy is used in diagnosis or therapy for inalignant tumors such as cancer. In this photoradiation therapy, a substance causing photosensitivity such as an organic pigment is selectively taken into tumor cells and is excited with low power level laser light irradiation so that the tumor cells can be killed. Theoretically, this photoradiation therapy has an advantage that only the tumor cells can be damaged due to the substance so that other normal cells are not damaged.

In the photoradiation therapy, the substance causing photosensitivity must have at least following conditions.

(1) It must have compatibility with the tumors.
(2) It must have photochemical reactivity.
(3) It must be able to be used in safety. (It must not have toxicity. It must be water-soluble and metabolic.)
(4) It must not remain in the tumor cells more than a predetermined time.
(5) It must be able to be produced repeatedly.
(6) It must have operating experience in clinic. (It must show medical effects without any accident.)

It is well known that pheophorbide a can be used as the substance causing photosensitivity. The pheophorbide a satisfies the above mentioned conditions except safety (3). Precisely, the pheophorbide a is not water-soluble so as to be deposited in a human body. Thereby, shock accidents may be caused. Accordingly, it has been impossible to use the pheophorbide a for the human body as it is.

Therefore, it is an important subject to give water-solubility to the pheophorbide a. In the prior art, the following is processes have been used in order to achieve this subject.

(a) The pheophorbide a is dissolved in dimethyl sulfoxide (DMSO) as an organic solvent. Then, this solution is diluted with a buffer solution of phosphoric acid so as to be used as the substance causing photosensitivity.

(b) The powder of the pheophorbide a is kneaded with a small amount of alkali solution. Then, the resultant pheophorbide a in the form of paste is diluted with a buffer solution of phosphoric acid so as to be used as the substance causing photosensitivity.

(c) The pheophorbide a is dissolved in albumin so as to be used as the substance causing photosensitivity.

(d) The pheophorbide a is dissolved in lipidol (oil) so as to be used as the substance causing photosensitivity.

However, the above processes have severe disadvantages respectively.

(a) The organic solvent, DMSO is very poisonous. Thus, this process has a deficiency in safety.
(b) After dilution, settlement is often caused, resulting in a deficiency in safety.
(c) The albumin often causes anaphylaxis shock. Thus, this process has also a deficiency in safety.
(d) Due to the character of the lipidol, it is impossible to use this substance in a vein. Accordingly, it can not be used for many kinds of therapy.

SUMMARY OF THE INVENTION

It is therefore a main object of the present invention to provide a producing method of pheophorbide a which is water-soluble and which can be used safely in the human body.

In order to overcome the above mentioned problems, the present invention provides a producing method of pheophorbide a comprising:

dissolving sodium hydroxide in one solvent selected from n-propyl alcohol, isopropyl alcohol and the mixture of n-propyl alcohol and isopropyl alcohol so as to prepare a solution of the sodium hydroxide;

dissolving the pheophorbide a into a solvent, which is miscible with the solvent selected from n-propyl alcohol, isopropyl alcohol and the mixture of n-propyl alcohol and isopropyl alcohol so as to prepare a solution of the pheophorbide a; and dissolving the solution of tile pheophorbide a in the solution of the sodium hydroxide so as to obtain sodium pheophorbide a.

In order to give water-solubility to the pheophorbide a, the pheophorbide a must react with the sodium hydroxide so as to form a salt. In this reaction, first, the sodium hydroxide is dissolved in a specific solvent A' so as to prepare the solution A. At the same time, the pheophorbide a is dissolved in a specific solvent B' so as to prepare the solution B. Then, the solution A is dissolved in the solution B. In this case, the solvent B' must be miscible with the solvent A'. Then, the solvents A' and B' must not react with the pheophorbide a, because molecule denaturation of the pheophorbide a should be prevented. Further, in order to separate the resultant sodium pheophorbide a from the mixture of the solutions A and B easily, the salt of the pheophorbide a must be water-insoluble so as to form precipitate.

According to the present invention, n-propyl alcohol and/or isopropyl alcohol is used as the solvent for the sodium hydroxide. Accordingly, in order to satisfy the above conditions, as the solvent for the pheophorbide a, well-known ether and the like can be used without the molecule denaturation of the pheophorbide a. As a result, the sodium pheophorbide a can be precipitated so as to be separated in ease.

Further objects and advantages of the present invention will be apparent from the following description, reference being had to the accompanying drawing wherein preferred embodiments of the present invention are clearly shown.

DESCRIPTION OF THE PREFERRED EMBODIMENT

Figure 1A:
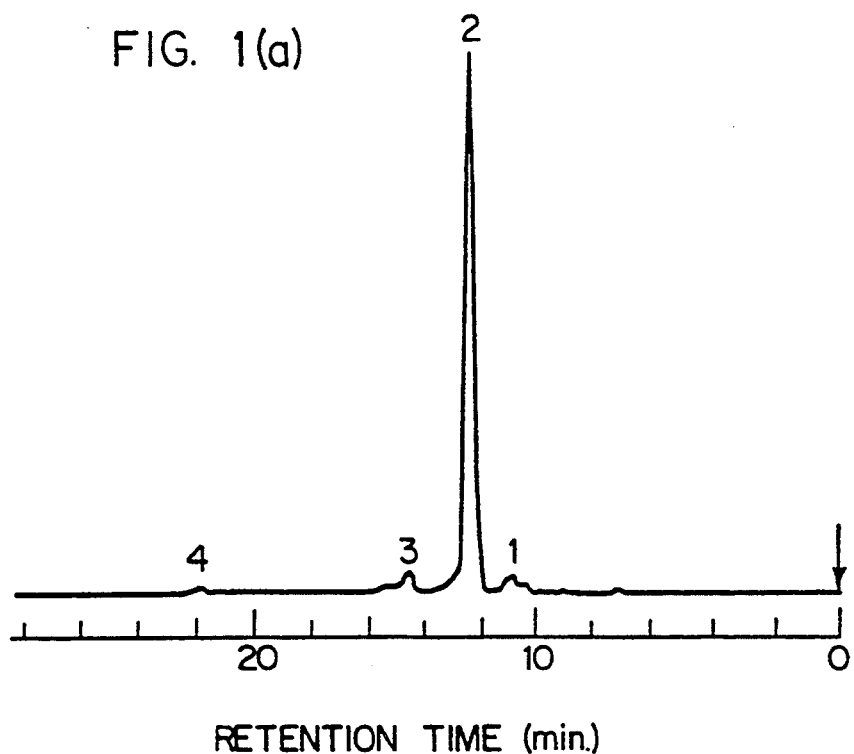
FIGS. 1(a)–(b) are HPLC analysis charts.

Now, the present invention is described more particularly.

As described above, in order to obtain the sodium salt of the pheophorbide a ($C_{32}H_{32}N_4O(COOH)$-$COOCH_3^+$), the solvent for the pheophorbide a must be miscible with the solvent for the sodium hydroxide. Further, the resultant sodium pheophorbide a must be insoluble in the solvents, because the precipitate must be obtained so as to be separated from the solvents. As the solvent for the pheophorbide a, which satisfies the above conditions, there can be mentioned ether, acetone, chloroform and the like. On the other hand, as the solvent for the sodium hydroxide, methyl alcohol and ethyl alcohol have been normally used.

However, it is well known that when the pheophorbide a reacts with methyl alcohol or ethyl alcohol in the presence of alkali. molecule denaturation of the pheophorbide a takes place vigorously so that oxidation of the pheophorbide a is accelerated. Accordingly, when the sodium salt of the pheophorbide a is obtained, it is most important to select the solvent for the sodium hydroxide, by which the oxidation is not accelerated.

Therefore, in tile present invention, n-propyl alcohol and/or isopropyl alcohol is used as the solvent for the sodium hydroxide. Due to the solvents, the sodium salt of the pheophorbide a can be obtained without the molecule denaturation of the pheophorbide a. Further, according to the present invention, the solution of the pheophorbide a can be prepared easily without dissolving auxiliary agent and particular dissolving technique.

EXAMPLE

1. Producing method of the sodium pheophorbide a.

First, 500 mg of pheophorbide a obtained by a known producing method (chlorophyll a in ether is demagnesiumed by concentrated hydrochloric acid and is dephytoled with hydrolysis) is dissolved in 300 ml of ether. On the other hand, 100 mg of sodium hydroxide is dissolved in 30 ml of n-propyl alcohol or isopropyl alcohol. Then, this n-propyl alcohol or isopropyl alcohol solution of the sodium hydroxide is dropped into the ether solution of the pheophorbide a while the ether solution is stirred. In this case, in order to know how the reaction proceeds, one drop of the resultant solution is put on a filter paper and whether the precipitation is formed or not is observed. The reaction is continued until the solution around the precipitation on the filter paper is colorless.

Next, the resultant solution containing the above precipitation (sodium pheophorbide a) is put in a tube of a centrifugal separator and separated centrifugally (2500 rpm, 2 min.). The supernatant liquid is removed. Then, the solid on the bottom of the tube is dried with a vacuum dryer. As a result, the sodium pheophorbide a in the form of powder can be obtained.

2. Preparation of tile solution dissolving the sodium pheophorbide a.

2 ml of distilled water is poured into about 10 mg of the sodium pheophorbide a and this mixture is shaken gently. Thus, the sodium pheophorbide a is dissolved until this mixture becomes a clear solution. The pH value of the solution is approximately 9.2 to 9.5. Continuously, the solution optionally should be diluted with the buffer solution (pH value is 7.4 or 7.8) of phosphoric acid until a predetermined concentration is obtained.

3. Identification of the sodium pheophorbide a with HPLC (High Performance Liquid Chromatography) analysis and absorption spectrum in ultraviolet and visible region.

The identification of the sodium pheophorbide a is carried out as follows.

The sodium pheophorbide a is desodiumed with diluted hydrochloric acid and is dissolved in ether. Then, for comparison two kinds of samples, this ether solution and the normally obtained pheophorbide a are analyzed with the HPLC analysis and absorption spectral analysis respectively.

Figure 1B:
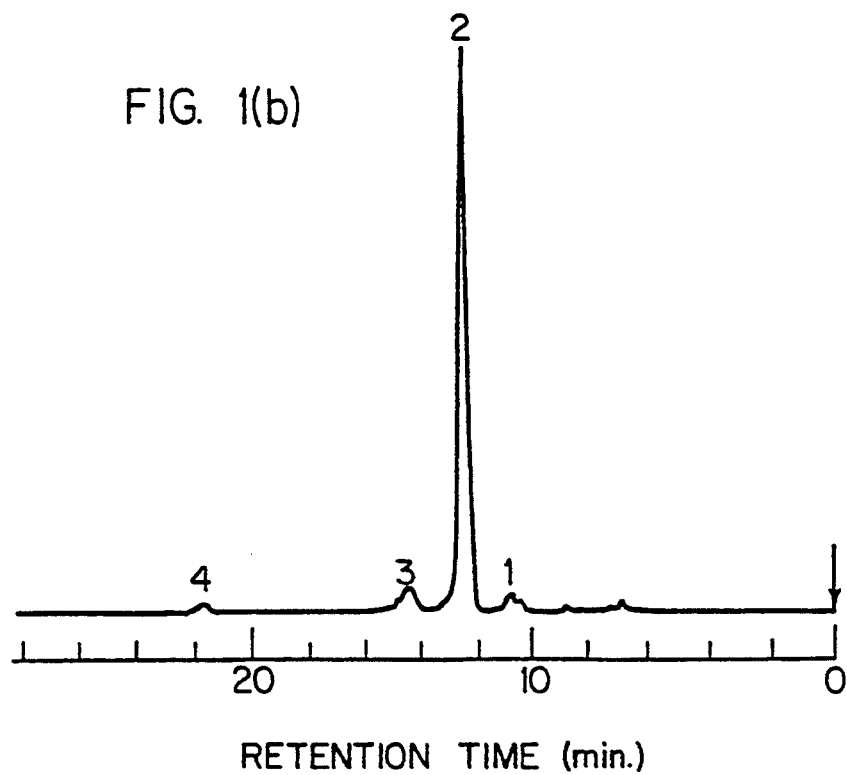

First, the HPLC analysis will be explained. As shown in FIG. 1, the chart (a) for the pheophorbide a and the chart (b) for the above ether solution are obtained. From these charts, the retention time of the ether solution is the same as that of the normally obtained pheophorbide a. Therefore, it is clear that the pheophorbide a exists in the ether solution. In FIG. 1, numerals 1, 2, 3 and 4 show the peak points of 10-OH pheophorbide a, pheophorbide a, pheophorbide a and pyropheophorbide a, respectively.

This HPLC analysis is carried out under following separating conditions.

column ... ODS SSC pack 4×250 mm
    eluate ... acetonitrile 0.1% phosphoric acid solution: tetrahydrofuran=88:10:2.
    rate of flow ... 1.0 ml/min.
    wave length ... 410 nm
    chart ... 0.5 cm/min.
    temperature ... 12° C.

Figure 2A:
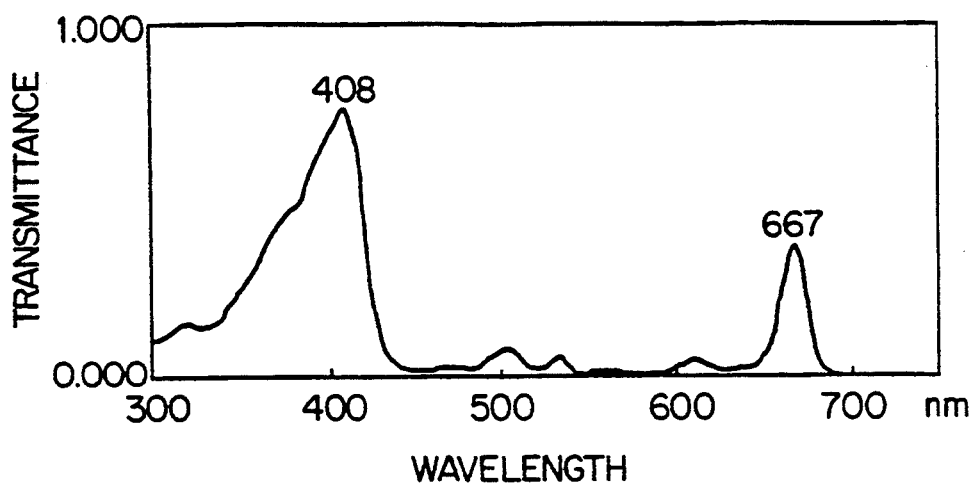
FIGS. 2(a)–(c) show absorption spectrum in ultraviolet and visible region.
Figure 2B:
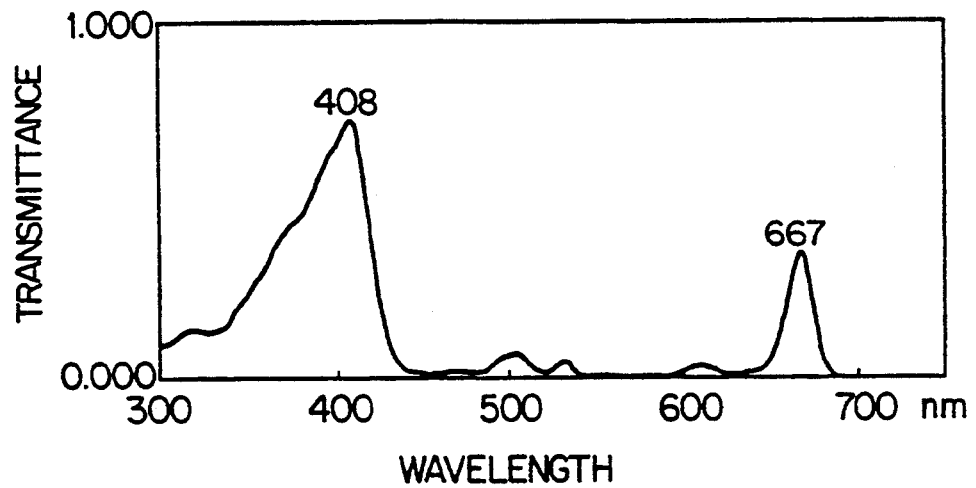
Figure 2C:
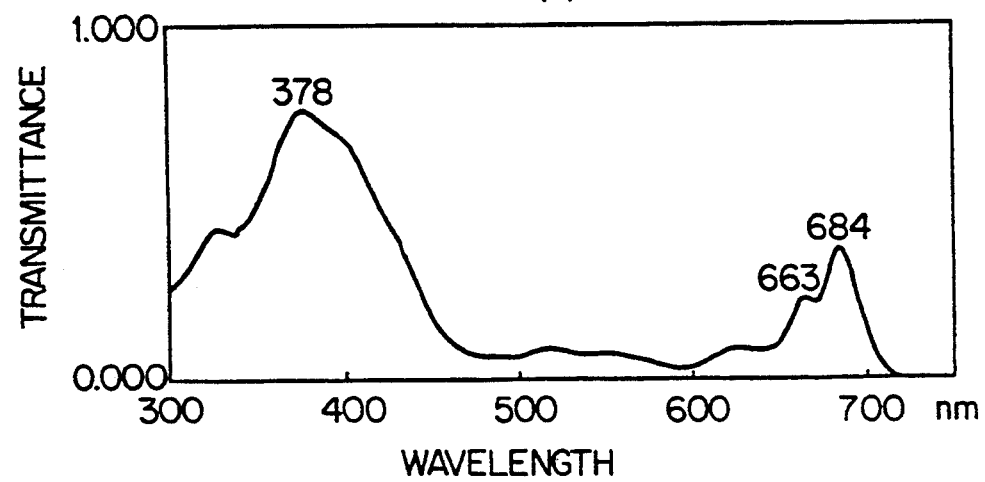

On the other hand, as shown in FIG. 2, the absorption wave length (a) of the ether solution is substantially the same as that (b) of the known pheophorbide a solution. Also from this, it can be confirmed that the pheophorbide a exists in the ether solution. For comparison, the absorption spectrum of the sodium pheophorbide a is shown in FIG. 2(C).

While preferred embodiments have been described, it is apparent that the present invention is not limited to the specific embodiments thereof.

What is claimed is:

1. A method of producing sodium pheophorbide a, comprising:
    dissolving sodium hydroxide in a solvent selected from the group consisting of n-propyl alcohol, isopropyl alcohol and a mixture of n-propyl alcohol and isopropyl alcohol to prepare a solution of the sodium hydroxide;
    dissolving pheophorbide a in a solvent which is miscible with said solvent selected from n-propyl alcohol, isopropyl alcohol and a mixture of n-propyl alcohol and isopropyl alcohol to prepare a solution of the pheophorbide a; and
    dissolving said solution of the pheophorbide a in said solution of sodium hydroxide to obtain sodium pheophorbide a.

2. A method as defined by claim 1, wherein the sodium pheophorbide a is obtained as a precipitate.

3. A method as defined by claim 2, including the further step of centrifugally separating the sodium pheophorbide a precipitate from the solvents.

4. A method as defined by claim 3, including the further step of drying the separated precipitate.

5. A method as defined by claim 1, wherein the pheophorbide a is dissolved in a solvent selected from the group consisting of ether, acetone and chloroform.

6. A method as defined by claim 1, wherein the sodium hydroxide solvent is n-propyl alcohol.

* * * * *